(12) United States Patent
Urey et al.

(10) Patent No.: US 9,810,632 B2
(45) Date of Patent: Nov. 7, 2017

(54) FLUORESCENT SUBSTANCE DETECTION SYSTEM

(71) Applicants: KUANTAG NANOTEKNOLOJILER GELISTIRME VE ÜRETIM A.S., İstambul (TR); KOÇ NIVERSITESI, Istanbul (TR)

(72) Inventors: Hakan Urey, Istanbul (TR); Osman Vedat Akgun, Istanbul (TR); Emre Heves, Istanbul (TR); Fehmi Civitci, Hillsboro, OR (US); Basarbatu Can, Istanbul (TR)

(73) Assignees: Kuantag Nanoteknolojiler Gelistirme vs Uretim A.S., Istanbul (TR); Koc Universitesi, Istanbul (TR)

( * ) Notice: Subject to any disclaimer, the term of this patent is extended or adjusted under 35 U.S.C. 154(b) by 0 days.

(21) Appl. No.: 15/326,995

(22) PCT Filed: Jul. 17, 2014

(86) PCT No.: PCT/TR2014/000301
§ 371 (c)(1),
(2) Date: Jan. 17, 2017

(87) PCT Pub. No.: WO2016/010494
PCT Pub. Date: Jan. 21, 2016

(65) Prior Publication Data
US 2017/0205346 A1    Jul. 20, 2017

(51) Int. Cl.
*G01N 21/64* (2006.01)
*G01N 21/85* (2006.01)

(52) U.S. Cl.
CPC ......... *G01N 21/643* (2013.01); *G01N 21/645* (2013.01); *G01N 21/8507* (2013.01);
(Continued)

(58) Field of Classification Search
CPC ............. G01N 21/6428; G01N 21/648; G01N 21/6486; G01N 21/645; G01N 2021/6484
See application file for complete search history.

(56) References Cited

U.S. PATENT DOCUMENTS

| 4,649,711 A | 3/1987 | Sibley et al. |
| 4,745,285 A * | 5/1988 | Recktenwald ..... G01N 21/6428 |
| | | 250/458.1 |

(Continued)

FOREIGN PATENT DOCUMENTS

| AU | 2012100395 A4 | 5/2012 |
| EP | 0257559 A2 | 3/1988 |

(Continued)

OTHER PUBLICATIONS

Hu, S.; Gao, X., Stable Encapsulation of Quantum Dot Barcodes with Silica Shells, Adv. Funct. Mater., 2010, 20, 3721-3726.

*Primary Examiner* — David Porta
*Assistant Examiner* — Faye Boosalis
(74) *Attorney, Agent, or Firm* — Halit N. Yakupoglu

(57) ABSTRACT

In the present invention, a fluorescent substance detection system (S) for detecting fluorescent substances in any environment is provided. Said detection system (S) comprises at least one illumination unit (1) which emits light to said environment in order to excite said substances; detection units (2), at least at a number equal to the number of types of fluorescent substances, for detecting emissions coming from said excited fluorescent substances and bandpass filters (3), each connected to detection units (2) one by one, wherein bandpass filters (3) have a center wavelength matched to the center emission wavelength of corresponding fluorescent substance.

30 Claims, 7 Drawing Sheets

(52) U.S. Cl.
CPC ............ *G01N 2021/6484* (2013.01); *G01N 2201/0826* (2013.01)

(56) References Cited

U.S. PATENT DOCUMENTS

| | | | |
|---|---|---|---|
| 5,229,298 | A | 7/1993 | Zoumalan |
| 5,279,967 | A | 1/1994 | Bode |
| 5,358,873 | A | 10/1994 | Nowak |
| 5,359,522 | A | 10/1994 | Ryan |
| 5,420,797 | A | 5/1995 | Burns |
| 5,525,516 | A | 6/1996 | Krutak et al. |
| 5,652,810 | A | 7/1997 | Tipton et al. |
| 5,710,046 | A | 1/1998 | Rutledge et al. |
| 5,723,338 | A | 3/1998 | Rutledge et al. |
| 5,742,064 | A | 4/1998 | Infante |
| 5,878,178 | A | 3/1999 | Wach |
| 5,878,772 | A | 3/1999 | Belyea |
| 5,928,954 | A | 7/1999 | Rutledge et al. |
| 5,958,780 | A | 9/1999 | Asher et al. |
| 6,274,381 | B1 | 8/2001 | Pauls et al. |
| 6,312,958 | B1 | 11/2001 | Meyer et al. |
| 6,576,155 | B1 | 6/2003 | Barbera-Guillem |
| 6,598,792 | B1 | 7/2003 | Michot et al. |
| 6,691,557 | B1 | 2/2004 | Rice |
| 6,692,031 | B2 | 2/2004 | McGrew |
| 6,881,381 | B1 | 4/2005 | Asher et al. |
| 7,466,400 | B2 | 12/2008 | Luther et al. |
| 7,763,469 | B2 | 7/2010 | Babichenko et al. |
| 8,158,432 | B2 | 4/2012 | Grof et al. |
| 8,384,891 | B2 | 2/2013 | Carr et al. |
| 8,574,323 | B2 | 11/2013 | Green et al. |
| 8,592,213 | B2 | 11/2013 | Wilkinson et al. |
| 8,744,723 | B2 | 6/2014 | Jones |
| 8,805,592 | B1 | 8/2014 | Booth et al. |
| 2002/0164271 | A1 | 11/2002 | Ho |
| 2004/0248307 | A1 | 12/2004 | Grof et al. |
| 2004/0262400 | A1 | 12/2004 | Chang et al. |
| 2005/0165554 | A1 | 7/2005 | Betancourt et al. |
| 2005/0241989 | A1 | 11/2005 | Sant et al. |
| 2005/0260764 | A1 | 11/2005 | Grigsby et al. |
| 2006/0118741 | A1 | 6/2006 | Ross et al. |
| 2006/0173362 | A1 | 8/2006 | Toms et al. |
| 2007/0064323 | A1 | 3/2007 | Luther et al. |
| 2007/0088600 | A1 | 4/2007 | Lichtinger et al. |
| 2007/0178596 | A1 | 8/2007 | Babichenko et al. |
| 2008/0002927 | A1 | 1/2008 | Furnish |
| 2008/0021983 | A1 | 1/2008 | Dodson |
| 2008/0215719 | A1 | 9/2008 | Swan |
| 2009/0289113 | A1 | 11/2009 | Vilnai et al. |
| 2009/0307032 | A1 | 12/2009 | Tribe et al. |
| 2009/0322544 | A1 | 12/2009 | McDowell |
| 2010/0089486 | A1 | 4/2010 | Koeninger et al. |
| 2010/0208243 | A1 | 8/2010 | Suzuki et al. |
| 2010/0222917 | A1 | 9/2010 | Bohlig et al. |
| 2010/0305885 | A1 | 12/2010 | Ganapathy et al. |
| 2011/0040503 | A1 | 2/2011 | Rogers et al. |
| 2011/0101094 | A1 | 5/2011 | Call |
| 2011/0120589 | A1 | 5/2011 | Evans |
| 2011/0130882 | A1 | 6/2011 | Perez |
| 2011/0177494 | A1 | 7/2011 | Ismagilov et al. |
| 2011/0229983 | A1 | 9/2011 | Wilkinson et al. |
| 2012/0034702 | A1 | 2/2012 | Croud et al. |
| 2012/0035442 | A1 | 2/2012 | Barman et al. |
| 2012/0054201 | A1 | 3/2012 | Fischer |
| 2012/0104278 | A1 | 5/2012 | Downing et al. |
| 2012/0205449 | A1 | 8/2012 | Lewis et al. |
| 2012/0301872 | A1 | 11/2012 | Tormod |
| 2013/0009119 | A1 | 1/2013 | Natan et al. |
| 2013/0155402 | A1 | 6/2013 | Walton et al. |
| 2013/0179090 | A1 | 7/2013 | Conroy et al. |
| 2013/0283893 | A1 | 10/2013 | Earl et al. |
| 2014/0170754 | A1 | 6/2014 | Liu et al. |
| 2014/0236444 | A1 | 8/2014 | Stefan et al. |
| 2015/0300983 | A1 | 10/2015 | Urey et al. |

FOREIGN PATENT DOCUMENTS

| | | |
|---|---|---|
| EP | 0358203 A1 | 3/1990 |
| EP | 0489347 A1 | 6/1992 |
| EP | 0935750 B1 | 4/2002 |
| EP | 1441227 A2 | 7/2004 |
| EP | 1794764 B1 | 7/2011 |
| FR | 2566909 A1 | 1/1986 |
| GB | 1596521 A | 8/1981 |
| WO | 9412874 A1 | 6/1994 |
| WO | 0177391 A1 | 10/2001 |
| WO | 02098199 A2 | 12/2002 |
| WO | 2006036388 A2 | 4/2006 |
| WO | 2008019448 A1 | 2/2008 |
| WO | 2009026665 A1 | 3/2009 |
| WO | 2009063471 A2 | 5/2009 |
| WO | 2009120563 A1 | 10/2009 |
| WO | 2010089587 A2 | 8/2010 |
| WO | 2011037894 A1 | 3/2011 |
| WO | 2011123938 A1 | 10/2011 |
| WO | 2011132079 A1 | 10/2011 |
| WO | 2013079974 A1 | 6/2013 |
| WO | 2013126028 A2 | 8/2013 |
| WO | 2014063725 A1 | 5/2014 |
| WO | 2014087359 A1 | 6/2014 |

\* cited by examiner

FLUORESCENT SUBSTANCE DETECTION SYSTEM

FIELD OF THE INVENTION

Present invention relates to a system and method for detection and identification of fluorescent substances in any environment.

BACKGROUND

Fluorescence is the emission of light by a substance that has absorbed light and in most cases the emitted light has a longer wavelength and lower energy than the absorbed light. Most commonly used fluorescent substances are fluorescent dyes or quantum dots. Limitations with organic fluorescent dyes can be explained as follows: they have absorbance at specific wavelengths, they require multiple excitation wavelengths if multiple dyes are used; their broad emission profile, which causes spectral overlap limiting the production of large number of optical codes including different dyes and lastly, their photo-bleaching, luminescence quenching and low molar extinction coefficient. Quantum dots (QDs), however, with their large absorbance cross-section, narrow symmetric emission band, high molar extinction coefficient, long luminescence, high quantum yield and high resistance to photo-bleaching presents a strong alternative for tagging against fluorescent dyes and colorants.

Fluorescence has many practical applications including fluorescent labeling, tagging, dyes, biological detectors and chemical sensors etc. It is common to use fluorescent substances for variety of fluid products. These fluorescent substances are mixed into the liquid products in the form of fluorescent dyes, quantum dots or colorants and they enable identification of the fluid using optical sensors. This is also a widely accepted methodology in biotechnology, where fluorescent labels are generally used for detection of a protein or other labeled molecule via a fluorescence microscope, flow cytometer or some other fluorescence reading instruments. Such methods can be useful in localization of a target within a cell, flow cytometry (FACS) analysis, western blot assays, and other immune-analytical methods. However the detection of fluorescent markers in these methods requires taking a sample from the fluid and analyzing it with a suitable bulky laboratory apparatus, which is referred to as off-line identification, and this approach is generally inconvenient and time consuming.

Fluorescent substances are also widely used for identification of goods. Tagging of products is highly desirable for manufacturers to solve the problem of identifying, tracking as well as to prevent counterfeiting, product adulteration, unauthorized distribution and sale of products as well as false liability based on product substitution. Fluorescent substances are usually blended in ink and applied to the solid products to create a hologram or a barcode. In some applications, fiber optic probes are used for optically reading the tags. Fiber optical probes introduce advantages of reading from a small volume and improving the sensitivity. However, in such application examples, the reading part includes spectrometer and computers as signal processing resulting in bulky systems.

Bulky readout apparatus that are used in the aforementioned applications are required for sensitive reading of the fluorescent substances in the sub-ppm concentration ranges. However, such bulky systems only allow off-line identification and this is not practical in most of the aforesaid applications. Compact, lightweight and mobile systems which have sensitivity levels better than the bulky systems are highly desirable for online and point of use identification applications in order to give instant results and transfer the results to allocated systems.

In addition to this, in most of the applications, fluorescent substances are blended into fluids which have also their own fluorescence such as ink, petroleum based products etc. A background fluorescence effect is well known for highly absorbent and fluorescent environment/mediums when their emission/absorbance spectrum overlaps with the fluorescent substance emission wavelengths. This leads to difficulties in detection and identification of fluorescent substances present in such mediums.

Fluorescent substances are used previously to tag liquid products and identify those using optical sensors. For instance, U.S. Pat. No. 6,312,958 B1 relates to a method of marking liquids and detecting markers in liquids by exciting fluorescent markers and collecting the emission data from them. In addition, U.S. Pat. No. 5,928,954 describes a method for tagging hydrocarbons and for detecting the presence of tagged hydrocarbons. It is also mentioned in this reference that hydrocarbons have fluorescence and it has to be minimized. In addition, it is mentioned that the excitation results Rayleigh scattering signal creating background interference. However, this invention involves bulky optic setups for reading that is not convenient for online and point of use detection. Also, the reference does not offer any solution for the background signals.

QDs and fluorescent dyes are used for security and identification applications in U.S. Pat. No. 6,692,031 B2, US 20040262400 A1 and U.S. Pat. No. 6,576,155 B1 references. These references blend fluorescent nanocrystals in ink and apply them for tagging solid products. Also, the references use different wavelengths and intensities in order to create a barcode. However, they do not give any information on the background effects or cross talk on multiple markers. Moreover, optical readings in these references comprise bulky and expensive optical setups. Although the US 20040262400 A1 uses a fiber optic sensor for excitation and collection, the apparatus has spectrometer and PC for signal processing that limits the point of use applications.

EP 1441227 A2 reference describes a method, measuring the QDs during the flow. In this reference, fluorescent nanoparticles are placed into beads. During the flow from a channel, beads are excited optically or electrically and their emissions are captured and processed to identify the tag. Effect of QDs with different wavelengths and the effects of the background are not taken into consideration.

Biological applications of fluorescent markers are also discussed in US 20060173362 A1 and WO 01077391 A1 references, in which they are used for identifying cells and for reading beads in multi-assay form respectively. Detection principles in these references are similar but they are mainly for tagging beads for biological applications. Also, they did not mention multiple wavelength fluorescent substance effects on each other, or background effects.

Moreover, sensitivity increase in fiber optical probes is desired in fluorescent substance detection. For instance, US 20080002927 A1 discusses various fiber optic probe assemblies for spectroscopic examinations of biological tissues in-vivo. U.S. Pat. No. 5,878,178 A1, on the other hand, discusses making the tip of the fiber cone in order to increase collection angle. Application of these fiber probes are mainly for biological imaging. US 20120301872 A1 also discusses to improve sensitivity in fluorescent microscopes by placing a retro reflector below the sample carrier. However these techniques will also improve the noise from the background and it is not discussed in these references.

In WO2008/019448 time gating is used for flow cytometry to capture only long lived fluorescence emission after auto-fluorescence has decayed away. However this is mainly used for flow cytometry and the system is bulky.

SUMMARY OF THE INVENTION

In the present invention, a fluorescent substance detection system for detecting fluorescent substances in any environment is provided. Said detection system includes at least one illumination unit which emits light to said environment in order to excite said substances; detection units, at least at a number equal to the number of types of fluorescent substances, for detecting emissions coming from said excited fluorescent substances and bandpass filters, each connected to detection units one by one, wherein bandpass filters have a center wavelength matched to the center emission wavelength of corresponding fluorescent substance.

Present invention relates to a real time and online detection and identification method for fluorescent substances in any environment and an apparatus which comprises highly sensitive and compact fiber optical detector that detects substances in highly fluorescent and highly absorbent environment and simultaneously transfer the reading to the signal processing unit.

Multiple fluorescent substances with different wavelengths and intensities in various mediums can be detected real time, in stationary or dynamic state using a very compact, highly sensitive and robust fiber optical sensor, even when the medium is absorbent and fluorescent.

The environment that contains fluorescent substances comprises highly absorbent, highly fluorescent, any type of liquid, any type of gas or any type of solid. The environment also comprises stationary and dynamic mediums.

To differentiate fluorescent substances from highly fluorescent and highly absorbent medium (background) is very critical issue. In the present invention, laser gating and dynamic background subtraction are implemented to remove the background noise. Furthermore, to increase the detection sensitivity in any medium during real time measurement, different collection enhancement parts are designed for the fiber optical probe. These parts comprise: retroscreen, concentrator and elliptical mirror. All these parts can be placed to the tip of the probe to increase the sensitivity of the fiber optical sensor.

The object of the invention is to provide a fluorescent substance detection system for detecting (identifying) fluorescent substances in any environment.

Other object of the present invention is to provide a fluorescent substance detection system wherein in-situ and real time detection (identification) are possible.

Figure 1:
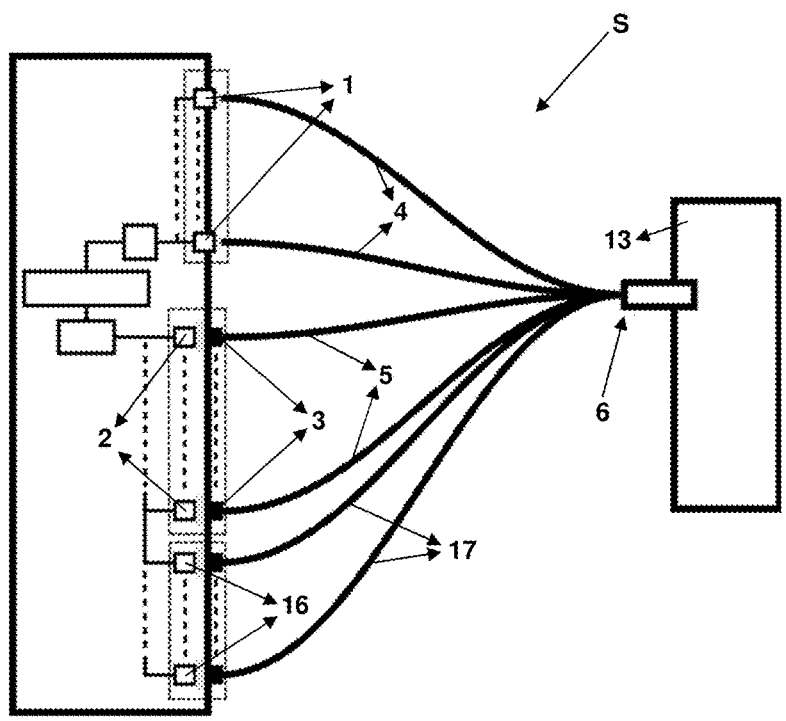
FIG. 1 shows an exemplary embodiment of the fluorescent substance detection system of the present application.
Figure 2:
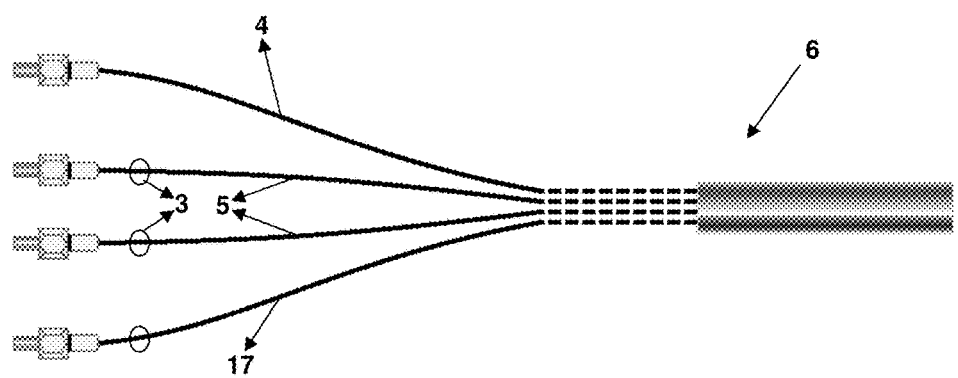
FIG. 2 shows an exemplary embodiment of a transmitting probe of the present application.
Figure 3:
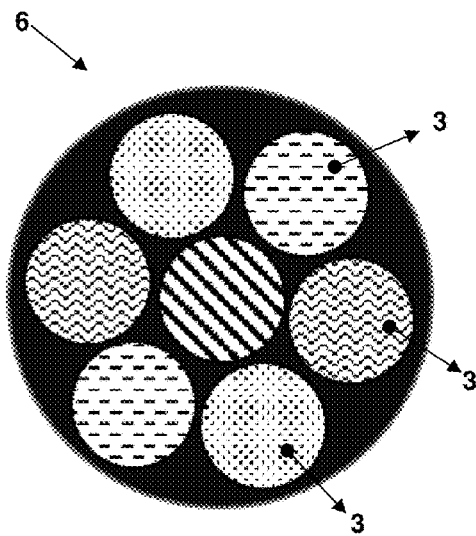
FIG. 3 shows a cross section view of the transmitting probe of the present application.
Figure 4:
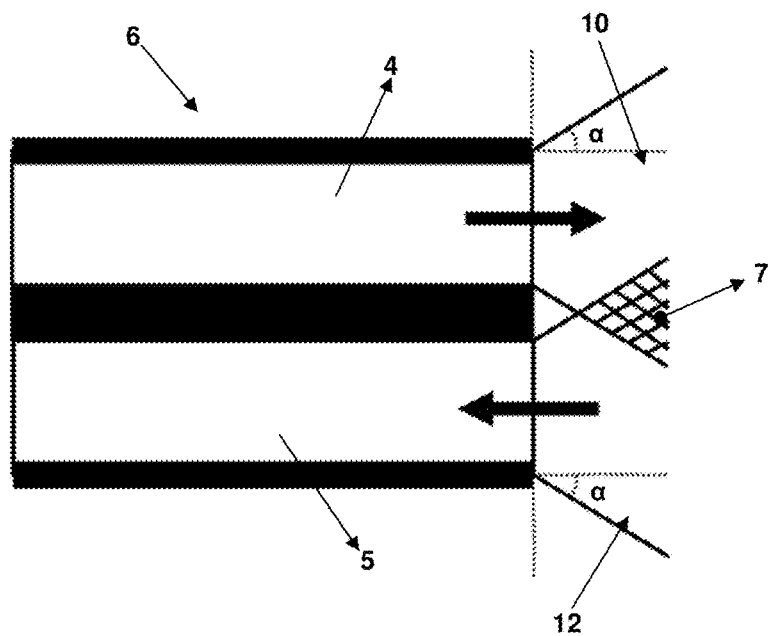
FIG. 4 shows another exemplary embodiment of a transmitting probe of the present application.

The features described in the present invention and the corresponding reference numerals are as follows:
Detection system (S);
Illumination unit (1);
Detection unit (2);
Bandpass filter (3);
Excitation transmitter (4);
Collection transmitter (5);
Imaginary collection transmitter (5');
Transmitting probe (6);
Intersection area (7);
Compound parabolic concentrator (8);
Original excitation cone (9);
Excitation cone (10);
Original collection cone (11);
Collection cone (12);
Measurement medium (13);
Reflective surface (14);
Background detector (16);
Background transmitter (17);
Opening half angle ($\alpha$);
Single transmitter (18);
Dichroic mirror (19); and
Collimation lens (20).

DETAILED DESCRIPTION OF THE INVENTION

Product counterfeiting and product adulteration are major problems in many areas of the world by damaging the reputation of the genuine product and causing a tax loss for governments. Therefore, checking and monitoring the authenticity of the products is utmost importance. For most of the products, authenticity is checked by security holograms. However, authenticities of the fluid materials, especially fuels, are not able to be checked using security holograms. In order to check authenticity of the fluids, fluorescent substances are mixed with fluids. By detecting the presence and/or quantity of said fluorescent substances in a material, authenticity of said material is able to be checked. In the present invention, a fluorescent substance detection system for detecting (identifying) fluorescent substances in any environment is provided.

Exemplary embodiments of the detection system (S) of the present invention are shown in FIGS. 1-9. Said detection system (S) detects each fluorescent substance having known discrete emission spectrums, existing as a mixture in an environment. Detection system (S) of the present invention comprises, at least one illumination unit (1) which emits light to said environment in order to excite said substances;

detection units (2), at least at a number equal to the number of types of fluorescent substances, for detecting emissions coming from said excited fluorescent substances and bandpass filters (3), each connected to detection units (2) one by one, wherein bandpass filters (3) have a center wavelength matched to the center emission wavelength of corresponding fluorescent substance; and at least one signal processing unit, connected to said detection units (2) receiving signals form them and process said signal to identify/quantify the fluorescent substances.

In an exemplary embodiment of the present invention, said illumination unit (1) emits light specific wavelength (such as ultraviolet, visible spectrum or infrared) to an environment, which comprises fluorescent substances having known discrete emission spectrums. Said fluorescent substances are excited by the emitted light. Emissions of the fluorescent substances are filtered by the bandpass filters (3). Therefore, each detection unit (2) receives emissions of only one substance. Then, each of said detection units (2) detect the presence and/or quantity of the fluorescent substances according to received emissions.

In a preferred embodiment of the present invention, light emitted from illumination unit (1) reaches to said environment by passing through the free space. Similarly, emissions of the fluorescent substances reach to the detection unit (2) by passing through the free space.

In another preferred embodiment, detection system (S) comprises at least one excitation transmitter (4) which transmits light emitted from illumination unit (1) reaches to said environment. Detection system (S) further comprises at least one collection transmitter (5) which transmits emissions of the fluorescent substances reach to the detection unit (2). Said excitation transmitter (4) and collection transmitter (5) are preferably in the form of fiber or any other light carrying material. Fiber diameters can vary over a selected range (10 μm to 2000 μm) but the number of the collection and illumination fibers should be arranged to achieve the maximum collection efficiency of the system.

In an exemplary embodiment of the present invention, said bandpass filters (3) are placed on said collection transmitters (5). In this embodiment, each of the collection transmitters (5) transmits emissions of only one fluorescent substance.

In another preferred embodiment of the present invention, said excitation transmitter (4), collection transmitter (5) and bandpass filter (3) are placed in a transmitting probe (6). Said transmitting probe (6) is connected to illumination unit (1) and detection unit (2) from one end and connected to a measurement medium (13) at other end. Said measurement medium (13) may be a closed medium (such as a can or bottle) or a flowing medium (such as fuel inlet of a vehicle), wherein a fluid comprising fluorescent substances. In this embodiment, by changing the transmitting probe (6), different fluorescent substances are able to be detected. Moreover, since measurement medium (13) is able to be a flowing medium, according to the present invention, in-situ and real time detection are possible.

The fluorescence information from the fluorescent substances in the medium is taken from the intersection of excitation cone (10) and collection cones (12) of the excitation transmitter (4) and collection transmitter (5). The volume of excitation cone (10) or collection cone (12) of the illumination or collection fiber is directly correlated by opening half angle (α) and the diameter of the excitation transmitter (4) and collection transmitter (5). As the opening half angle (α), which is in the range of 10°-60°, or said diameter increases, the volume of the intersection area (7); hence the signal to noise ratio of the system increases. The intersection area (7) volume also increases by decreasing the distance between excitation transmitter (4) and collection transmitter (5), which is limited by the thickness of the transmitter cladding. The cladding thickness is directly correlated with fiber diameter, fiber and cladding material and NA value and can be as low as a couple of microns.

Illumination unit (1) comprises at least one light source for exciting the fluorescent substances in the environment. Illumination unit (1) may also comprise at least one driver circuit for light source to provide stable illumination power. Light source may be, but not limited to, laser diode and light emitting diode. Excitation wavelength of the light source is selected by taking into consideration of the emission wavelengths of the fluorescent substance(s) and the absorption behavior of the environment. Excitation wavelength of the light source must be in the range of the absorbance spectra of the fluorescent substance(s) and also must be different from emission wavelength of the fluorescent substance(s) in order to be able to differentiate fluorescent light from the excitation light. In addition to that, to excite more fluorescent substance(s), the excitation wavelength of the light source should be selected to avoid the absorbance of the environment.

Power stability of the light source is a crucial parameter in present invention and driver circuit can be utilized to avoid the fluctuations in the excitation power. Any fluctuation of the excitation power can lead to anomaly in detection of fluorescent substances. Because of that, illumination unit (1) preferably comprises backfacet photodiode to monitor the output power of the light source. The power driver circuit receives the power information of the light source from backfacet photodiode and serves as a feedback loop to adjust the supply of the light source to maintain output power stability.

Figure 13:
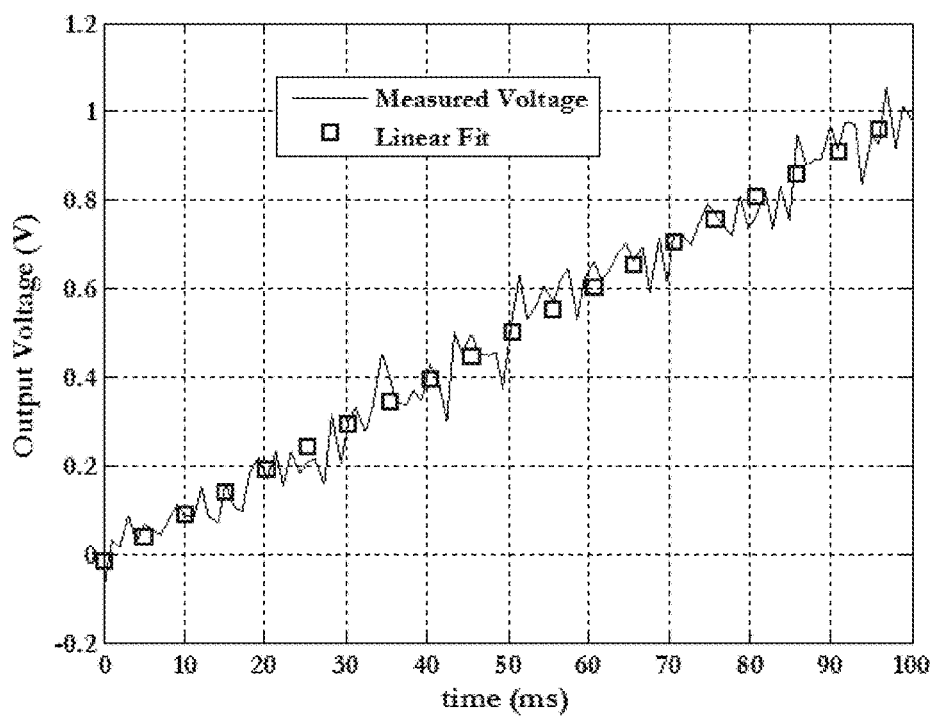
FIG. 13 shows output voltage vs. time graph of integration capacitor.

Detection unit (2) preferably comprises photodetector read out circuitry. Readout circuitry converts the signal coming from the photodetectors to meaningful information which can be processed (preferably by a signal processing unit). Signal value directly depends on the concentration of the fluorescent substances. In order to detect very low fluorescent substance concentrations, the readout circuit should be able to achieve high gain with a reasonable SNR value. This is mainly achieved by capacitive integration. Therefore, in a preferred embodiment, said detection unit (2) comprises at least one integration capacitor, which filters small fluctuations on the signal coming from said photodetectors. Detector signal is integrated at the capacitor. As the capacitor charges, its voltage increases linearly with some fluctuations. In order to achieve higher SNR, linear fitting is applied to the increasing voltage waveform by calculating its least squares regression line. Slope of the linear fit is multiplied by the integration time to calculate the integrated signal. An exemplary case is shown in FIG. 13. Capacitance value is 10 pF, integration time is 100 ms and current to be measured is 100 pA. As seen from the FIG. 13, by using linear fit algorithm, it is possible to get rid of small fluctuations to achieve high SNR.

Figure 5:
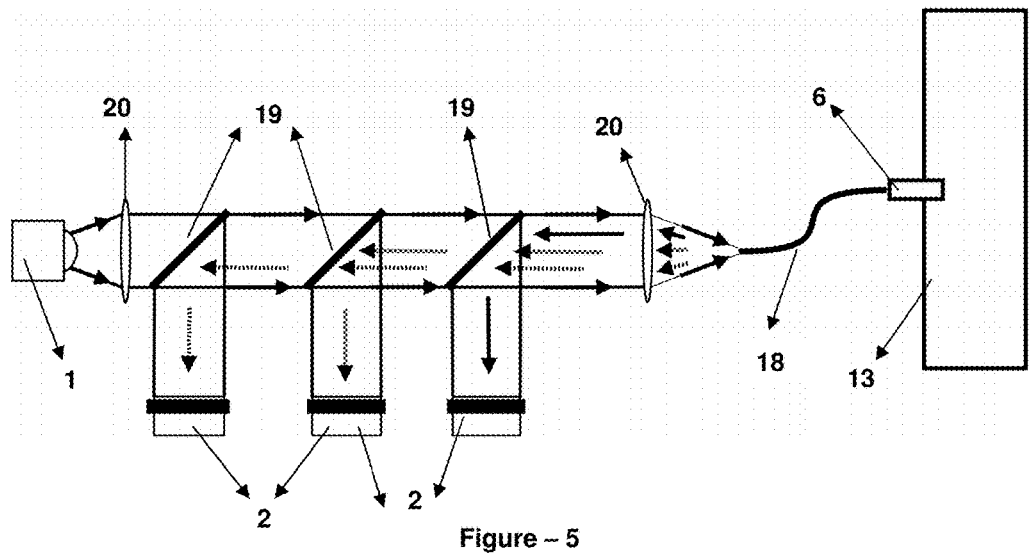
FIG. 5 shows another exemplary embodiment of a transmitting probe of the present application.

In another preferred embodiment, shown in FIG. 5, detection system (S) comprises a single transmitter (18) that is both used for transmitting light emitted from illumination unit (1) reaches to said environment and transmitting emissions of the fluorescent substances reach to the detection unit (2). The collected fluorescence from different wavelength fluorescent substances are separated using dichroic mirrors (19) in this configuration.

Dichroic mirror (19) is an optical filter, which transmits a specified wavelength band of light and reflects the remaining, at its operating bandwidth. Number of the dichroic mirrors in the system equals to one less than the sum of the number of different wavelength fluorescent substances and the reference wavelengths for background fluorescence that is desired to be monitored. Mirrors are positioned in a way that they make 45 degree with the main optical axis. Light collected from the single transmitter is collimated using lens (20). Collimated light passes through the dichroic mirrors. At each incidence on dichroic mirror, a desired spectral band of the light is reflected and collected by the detection unit. Output of each detection unit carries the concentration information of different wavelength fluorescent substances.

Figure 6:
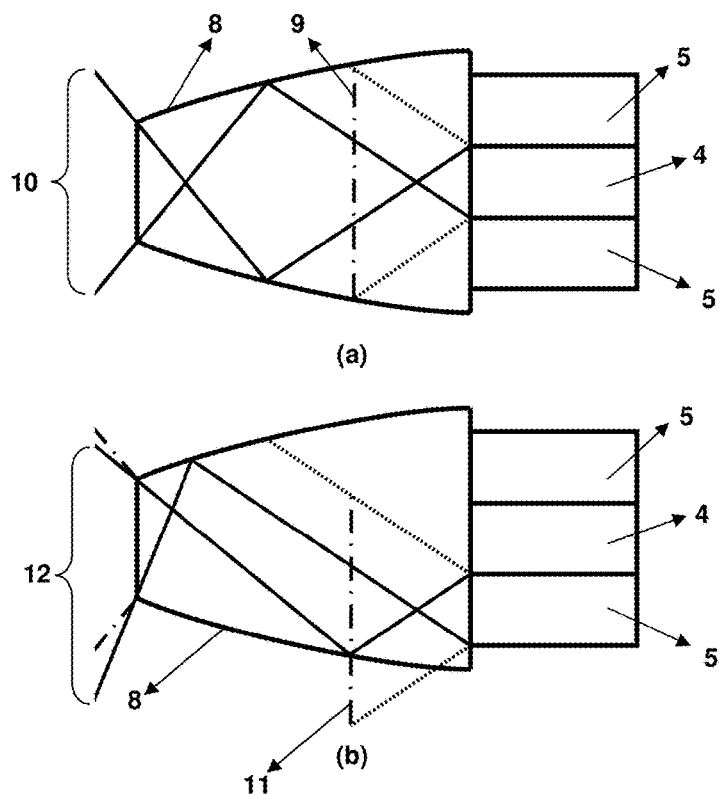
FIG. 6 shows another exemplary embodiment of a transmitting probe of the present application.

In another preferred embodiment of the present invention, shown in FIG. 6, the collection efficiency of the transmitting probe (6) is able to be increased by using non-imaging optical element called compound parabolic concentrator (8). Usually, compound parabolic concentrators (8) are used for collecting light from a large area with a limited acceptance angle and concentrate the collected light into a small area. Here, it is used in the reverse direction: The large area facet of the compound parabolic concentrator (8), which has an acceptance angle equal to the acceptance angle of the collection transmitters (5), is attached to the transmitting probe (6) and the small area facet is immersed in the medium. Preferably, a hollow compound parabolic concentrator (8) is used for medium since there will be extra fluorescence light collection from the inner side of the compound parabolic concentrator (8). As can be seen in FIG. 6, the compound parabolic concentrator (8) expands both the excitation and collection cones, which results in excitation of more fluorescent particles and collection from a larger volume in the medium. In other words, excitation cone (10) becomes larger than the original excitation cone (9) and collection cone (12) becomes larger than original collection cone (11). Furthermore, the overlap between excitation cone (9) and collection cones (10) is increased at the exit of the compound parabolic concentrator (8), which increases the collection efficiency.

Figure 7:
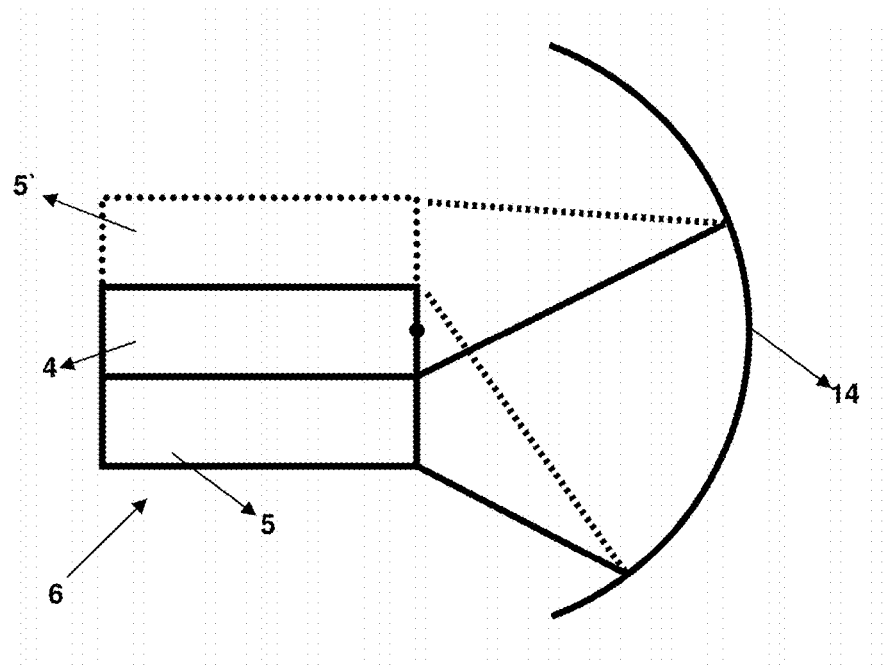
FIG. 7 shows another exemplary embodiment of a transmitting probe of the present application.
Figure 8:
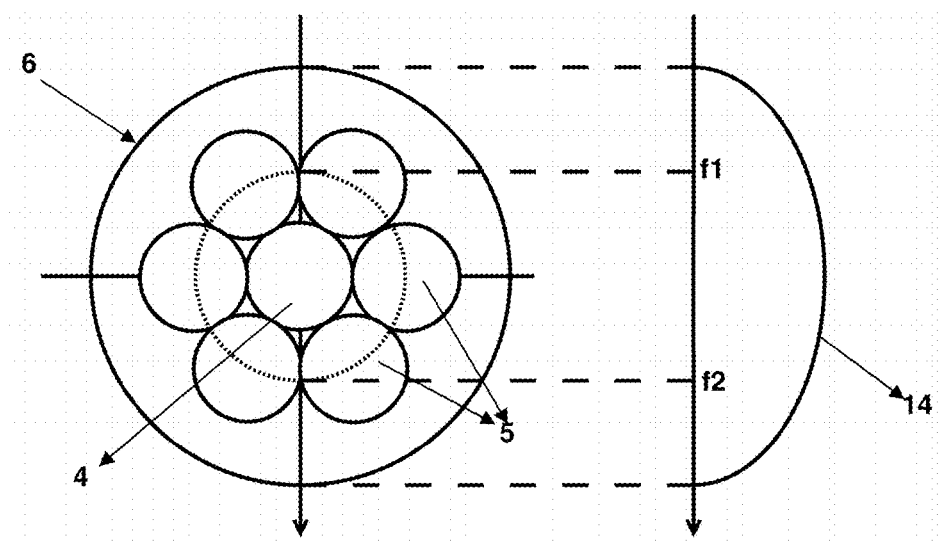
FIG. 8 shows another exemplary embodiment of a transmitting probe of the present application.

In another preferred embodiment, shown in FIGS. 7 and 8, the fluorescence light that scatters away from the collection transmitters (5) can be directed back to the collection transmitters (5) by using a reflective surface (14). Preferably, said reflective surface (14) is a retroreflective surface. FIG. 7 shows the cross section of such a configuration: a spherical mirror (as reflective surface (14)), which has a focal point at the center point of the excitation transmitter (4) exit, creates an imaginary collection transmitter (5') facet at the other side of the excitation transmitter (4). The imaginary collection transmitter (5') has its own collection cone in addition to the original collection cone of the collection transmitter (5). The imaginary collection transmitter (5') increases the collection efficiency of the detection system (S). Furthermore, the excitation light turns back to the excitation transmitter (4) after hitting the reflective surface (14) and results in double illumination of the medium that contains fluorescent substances.

As shown in FIG. 8, said reflective surface (14) may be in the form of an elliptical mirror. In this embodiment, focal points (f1, f2) of the elliptical mirror are on a circle corresponding to the trajectory of focal points of the rotated ellipse. As can be seen in FIG. 8, the collection transmitters (5) are positioned on the circle of focal points (f1, f2) and the excitation transmitter (4) is positioned at the center of the collection transmitters (5). Similar to the spherical mirror case, each collection transmitter (5) has images on the other collection transmitters (5) and these images create extra collection cones (10), which increase the collection efficiency of the detection system (S). Moreover, the excitation light reflected back towards the excitation transmitter (4) allows double illumination of the medium that contains fluorescent substances.

In another preferred embodiment of the present invention, detection system (S) comprises at least one background detector (16). Said background detector (16) detects the background emission of the measurement medium (13). Therefore, during the detection of the emissions of the fluorescent substances at the detection unit (2), effect of the background emission is reduced. In this embodiment, detection system (S) may further comprises at least one background transmitter (17), which transmits emissions of the background of the measurement medium (13) to the background detector (16). Said background transmitter (17) is preferably in the form of fiber in the transmitting probe (6).

In another preferred embodiment of the present invention, said signal processing unit receives signals from detection unit (2) and background detectors (16), process the signals to extract the signal coming from fluorescent substances only and calculates the quantity of the fluorescent substances in the medium. If the fluorescent substances are used for coding by employing different emission wavelengths and intensity levels, signal processing unit is used to decode the coding information in order to identify the medium. Present invention employs a new method for eliminating background signals, called as "dynamic background subtraction" and this method is employed by signal processing unit.

An approach of removing the background fluorescence of the medium is to measure the fluorescence of the medium before adding fluorescent substances and keeping this measurement result as a background reference value. Then this background reference value can be subtracted from the measurement results of the medium that contains fluorescent substances. However, it is observed that, the strength of the background fluorescence of the medium changes by adding the one or more fluorescent substances (having different wavelengths or different concentrations). This change in the background is related to:
  (i) absorption of the medium fluorescence by fluorescent substances,
  (ii) absorption of fluorescent substances fluorescence by the medium, and
  (iii) the decrease in the mean free path of the excitation light photons by addition of fluorescent substances.

Figure 9:
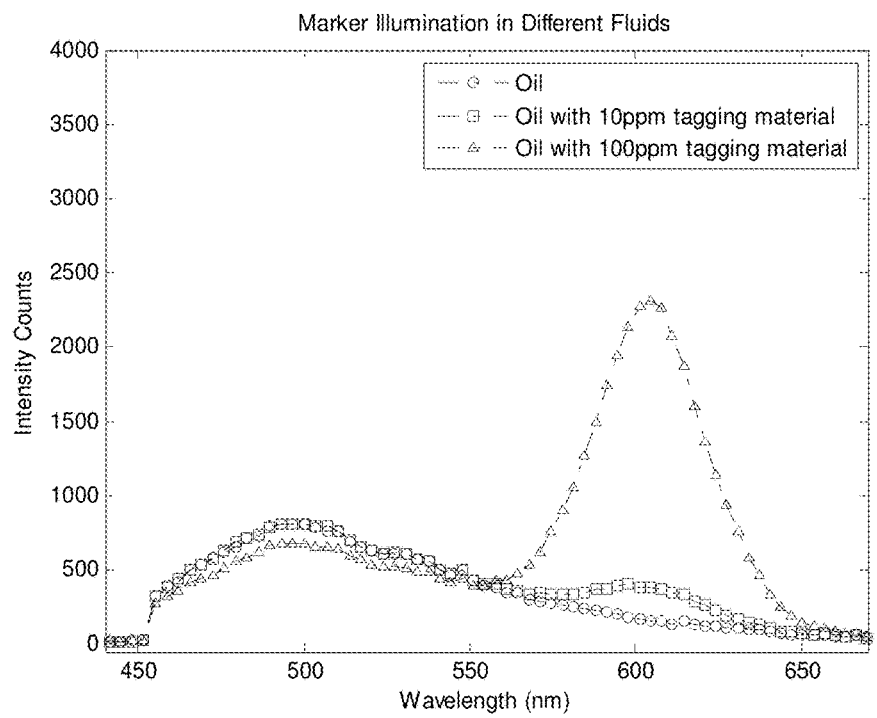
FIG. 9 shows wavelength versus intensity graph for oil, oil with 10 ppm tagging material and oil with 100 ppm tagging material.

An example of this effect is shown in FIG. 9. In the figure it can be seen that when the concentration of the fluorescent substances are increased, spectrum of the medium changes. Non-linear relation between luminescence intensity and the concentration can also be seen from the figure. When 10 ppm fluorescent substance is added to the medium, collected signal is around 400 but, luminescence intensity is not proportional to the concentration.

Since the first approach is insufficient to remove the background effects due to the aforementioned complex effects, according to the present invention a dynamic background subtraction method is provided. This method is related to real-time monitoring the fluorescence of the medium using single or multiple background detectors (16) and background transmitters (17) and calculating the real effect of the background fluorescence of the medium at the emission wavelengths of fluorescent substances present in the medium. Following this the calculated background fluorescence at the specific wavelength is subtracted from the reading at this wavelength and the real value of the fluorescent substance emission can be calculated. This operation is repeated for different wavelength fluorescent substances present in the medium.

Figure 10:
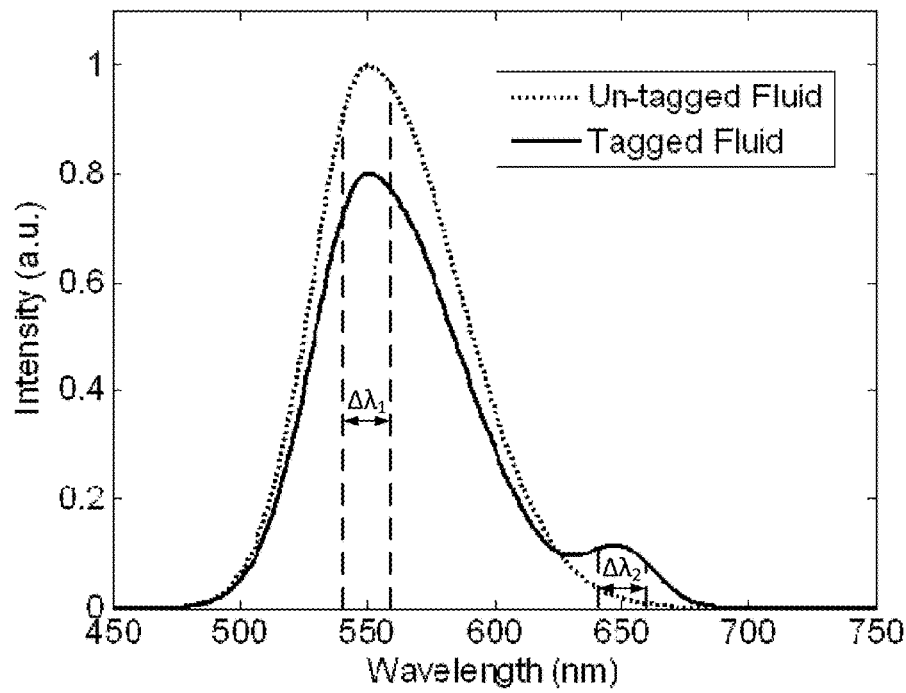
FIG. 10 shows wavelength versus intensity graph for untagged fluid and tagged fluid.

In one embodiment of the present invention, the procedure for dynamic background subtraction method using the background transmitter (17) for single wavelength fluorescent substance can be explained as follows. Note that the same procedure can be used in a parallel manner if multiple fluorescent substances are present in the medium. FIG. 10 shows the emission spectrums for blank medium and medium that contains fluorescent substances excited by same illumination conditions. The pass band of the optical filters for the reference fiber and one of the collection fiber are shown by $\Delta\lambda 1$ and $\Delta\lambda 2$ respectively. As can be seen from the figure, the background fluorescence power in $\Delta\lambda 1$ changed in the medium that contains fluorescent substance for one of the reasons explained above. Assuming that the emission spectrum trend of the medium is fixed, real power from the fluorescent substance (Pt) can be found by:

$$P_t = \left(\frac{P_{f0}}{P'_f}\right) P'_t - P_{bg0},$$

where Pbg0 is the power from the blank medium in the pass band $\Delta\lambda 2$, Pf' is the power from medium that contains fluorescent substance in the pass band $\Delta\lambda 1$, Pf0 is the power from the blank medium in the pass band $\Delta\lambda 1$ and Pt' is the power from the medium that contains fluorescent substance in the pass band $\Delta\lambda 1$.

Figure 11:
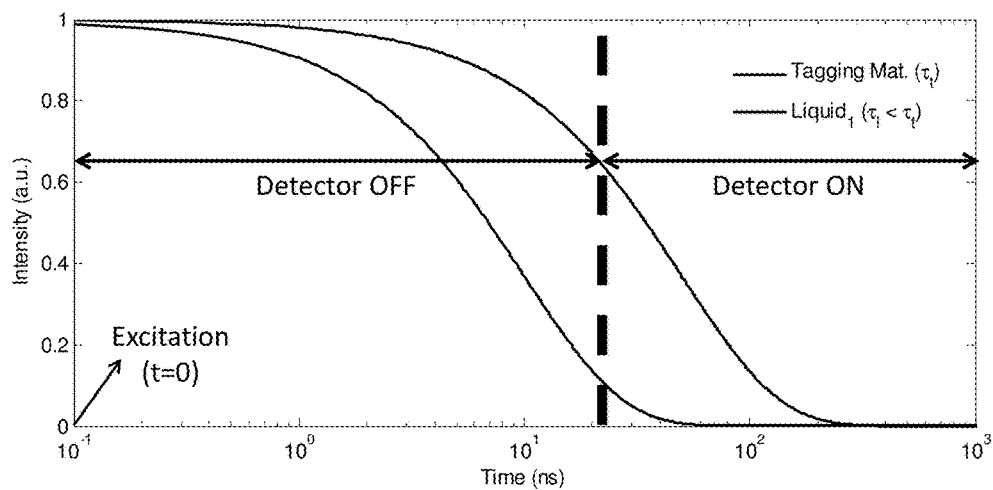
FIG. 11 shows ON and OFF states of the detector when $\tau1$ is shorter than it.
Figure 12:
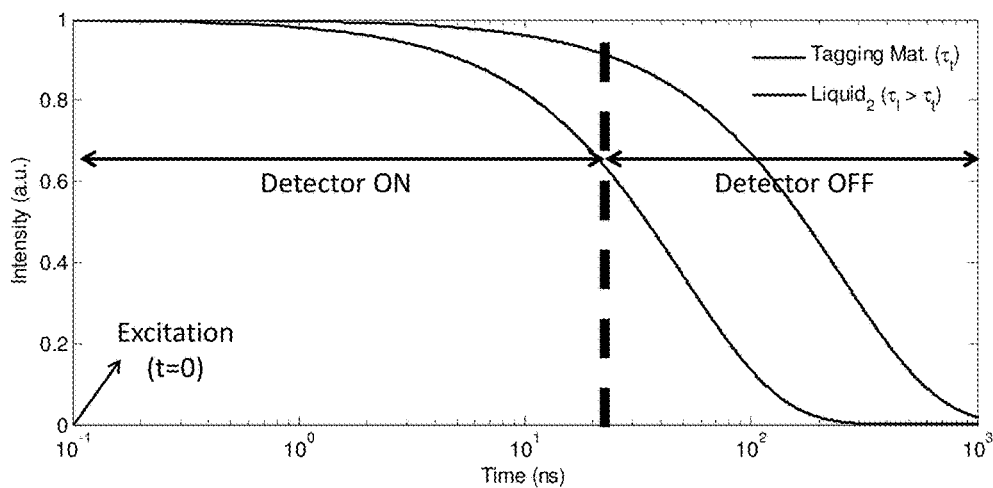
FIG. 12 shows ON and OFF states of the detector when $\tau1$ is longer than it.

In another embodiment electronic time gating is used for background subtraction. The emission wavelength of the fluorescent substances may overlap with the fluorescence spectrum of the medium. The intensity of this background fluorescence can be larger than that of the signal coming from the fluorescent substances, since the fluorescent substances are usually used in very small concentrations (sub-ppm level). In such a case, simple background subtraction can be insufficient if the background fluctuation is higher than the signal coming from the fluorescent substances. The background fluorescence can be partially removed by using electronic time gating if the fluorescence lifetime of the medium ($\tau 1$) and the fluorescent substances ($\tau t$) are different from each other. The electronic time gating method can be explained as follows. The sample is illuminated by a pulsed light source coupled to the fiber probe. The source has a pulse duration shorter than the fluorescence lifetimes of the medium and the fluorescent substances. The pulse duration is chosen very short (femtosecond level) since the fluorescence intensities of the medium and fluorescent substances cannot be separated for the period of pulse duration. The collected fluorescence from the medium is directed through the fiber probe to the detector synchronized with the light source. As can be seen in FIG. 11, If $\tau 1$ is shorter than $\tau t$, the detector is kept blind for a while after the excitation so that the fluorescence of the medium decays. The detector is activated before the fluorescence of the fluorescent substances totally decays. Here, the detector and its readout are chosen fast enough to make the necessary electronic switching possible. FIG. 12 shows the case when $\tau 1$ is longer than $\tau t$; The detector is activated just after the excitation and kept blind after a while in order to reject background fluorescence.

We claim:

1. A detection system adapted to detect tagging materials added in a tagged fluid in order to identify the tagged fluid, wherein the tagging materials are fluorescent substances having known discrete emission spectrums, existing as a mixture in the tagged fluid, wherein each of the fluorescent substances is used for coding information by employing different emission wavelengths and intensity levels to identify the tagged fluid which is highly absorbent and highly fluorescent, the detection system comprising:
    at least one illumination unit which emits light to the tagged fluid in order to excite the fluorescent substances to generate discrete emission spectrums used for generating coding information, the light emitted from the at least one illumination unit also generating fluorescence emissions in the tagged fluid along with the discrete emission spectrums from the fluorescent substances;
    detection units, at least at a number equal to the number of types of the fluorescent substances, for detecting emissions coming from the fluorescent substances;
    bandpass filters paired with the detection units, wherein the bandpass filter of each detection unit matches a center emission wavelength of the discrete emission spectrum of one of the fluorescent substances;
    at least one signal processing unit, connected to the detection units, to receive signals including the discrete emission spectrums of the fluorescent substances from the detection units and process the signals to decode the coding information in order to identify the tagged fluid; and
    at least one background detector for detecting the fluorescent emissions of the tagged fluid, the at least one background detector being in connection with the at least one signal processing unit to apply dynamic background subtraction method to extract the fluorescent emissions only from the fluorescent substances and employ them to identify the tagged fluid.

2. The detection system of claim 1, wherein light emitted from the at least one illumination unit reaches to the tagged fluid by passing through the free space.

3. The detection system of claim 1, wherein emissions of the fluorescent substances reach to the detection unit by passing through the free space.

4. The detection system of claim 1 further comprising at least one excitation transmitter which transmits light emitted from the at least one illumination unit to the tagged fluid.

5. The detection system of claim 4 further comprising at least one collection transmitter which transmits emissions of the fluorescent substances to the detection unit.

6. The detection system of claim 5, wherein the at least one excitation transmitter and the at least one collection transmitter are in the form of light carriers.

7. The detection system of claim 6, wherein the at least one excitation transmitter and the at least one collection transmitter are in the form of fiber.

8. The detection system of claim 5, wherein the bandpass filters are coupled with the at least one collection transmitter.

9. The detection system of claim 5 further comprising a transmitting probe, wherein the at least one excitation transmitter, the at least one collection transmitter and the bandpass filters are placed in the transmitting probe.

10. The detection system of claim 9, wherein the transmitting probe comprises a compound parabolic concentrator.

11. The detection system of claim 1, wherein the at least one illumination unit comprises at least one light source for exciting the fluorescent substances.

12. The detection system of claim 11, wherein the at least one illumination unit further comprises at least one driver circuit for controlling the at least one light source.

13. The detection system of claim 12, wherein the at least one illumination unit further comprises a photodiode to monitor the output power of the at least one light source.

14. The detection system of claim 1, wherein the detection units comprise a photodetector read out circuitry.

15. The detection system of claim 1, wherein the detection units comprise at least one integration capacitor, which filters small fluctuations on the signal coming from the photodetector read out circuitry.

16. The detection system of claim 1 further comprising a single transmitter which is both used for transmitting light emitted from the at least one illumination unit to reach the tagged fluid and transmitting emissions of the fluorescent substances to reach the detection units.

17. The detection system of claim 16 further comprising dichroic mirrors for separating light from the at least one illumination unit and different wavelength fluorescent substances.

18. The detection system of claim 1 further comprising a reflective surface as the tagged fluid.

19. The detection system of claim 18, wherein the reflective surface is a spherical mirror.

20. The detection system of claim 18, wherein the reflective surface is an elliptical mirror.

21. A method for real time and online identification of a tagged fluid which is highly absorbent and highly fluorescent, the tagged fluid including tagging materials added in order to identify the tagged fluid, wherein the tagging materials are fluorescent substances mixed in the tagged fluid in order to identify the tagged fluid, and wherein the fluorescent substances are used for coding information by employing different emission wavelengths and intensity levels to identify the tagged fluid, the method comprising:

illuminating the tagged fluid containing the fluorescent substances with at least one illumination unit to generate fluorescence emissions, from the fluorescent substances and the tagged fluid, including discrete emission wavelengths from the fluorescent substances;

collecting the fluorescence emissions from the tagged fluid and the fluorescent substances;

detecting the discrete emission wavelengths using at least one detection unit by filtering the fluorescence emissions from the fluorescent substances using a bandpass filter;

transferring the readings of the at least one detection unit, including the fluorescence emissions from the fluorescent substances, to a signal processing unit;

collecting the fluorescence emissions of the tagged fluid through a background transmitter;

detecting the fluorescence emissions of the tagged fluid by filtering specific emission wavelengths and using a background detector; and transferring the readings to the signal processing unit to apply dynamic background subtraction method for extracting the fluorescence emissions emitted from the fluorescent substances only to decode the coding information in order to identify the tagged fluid.

22. The method of claim 21, wherein the dynamic background subtraction method comprises:

measuring the fluorescence emissions of the tagged fluid using the background detector, calculating the effect of the fluorescence emissions of the tagged fluid at the discrete emission wavelengths of the fluorescent substances, and subtracting the effect of the fluorescence emissions of the tagged fluid at the discrete emission wavelengths of the fluorescent substances from the fluorescent substance emission measurement to extract the emissions coming from the fluorescent substances only.

23. The method of claim 22, wherein in the detecting step, linear fitting algorithm is applied to the increasing voltage waveform by calculating least squares regression line of the voltage.

24. The method of according to claim 22, wherein the tagged fluid is a liquid or gas medium.

25. The method of claim 22, wherein the tagged fluid is stationary or dynamic.

26. The method of claim 22, wherein the fluorescent substances are one or more organic light emitting molecules.

27. The method of claim 22, wherein the fluorescent substances are one or more quantum dots.

28. The method of claim 22, wherein the fluorescent substances are a combination of one or more organic light emitting molecules and one or more quantum dots.

29. The method of claim 22, wherein the fluorescent substances have a size between 10 to 1000 nm.

30. The method of claim 22, wherein the fluorescent substances have different emissions between 200-2000 nm.

* * * * *

UNITED STATES PATENT AND TRADEMARK OFFICE
CERTIFICATE OF CORRECTION

PATENT NO. : 9,810,632 B2
APPLICATION NO. : 15/326995
DATED : November 7, 2017
INVENTOR(S) : Hakan Urey et al.

It is certified that error appears in the above-identified patent and that said Letters Patent is hereby corrected as shown below:

On the Title Page

Item (71):
The first Applicant's name should read: -- KUANTAG NANOTEKNOLOJILER GELISTIRME VE URETIM A.S. --.

Item (71):
Delete "Istambul", and insert -- Istanbul --, therefor.

Item (71):
The second Applicant's name should read: -- KOC UNIVERSITESI --.

Item (73):
The first Assignee's name should read: -- Kuantag Nanoteknolojiler Gelistirme ve Uretim A.S. --.

Signed and Sealed this
Nineteenth Day of June, 2018

Andrei Iancu
*Director of the United States Patent and Trademark Office*